United States Patent [19]

Gianturco

[11] Patent Number: 4,494,531
[45] Date of Patent: Jan. 22, 1985

[54] EXPANDABLE BLOOD CLOT FILTER

[75] Inventor: Cesare Gianturco, Champaign, Ill.

[73] Assignee: Cook, Incorporated, Bloomington, Ind.

[21] Appl. No.: 447,420

[22] Filed: Dec. 6, 1982

[51] Int. Cl.³ .................... A61M 29/00; A61B 19/00
[52] U.S. Cl. .............................. 128/1 R; 128/303 R; 128/325
[58] Field of Search ............ 128/1 R, 325, 345, 303 R

[56] References Cited

U.S. PATENT DOCUMENTS

| 3,540,431 | 11/1970 | Mobin-Uddin | 128/1 R |
| 3,868,956 | 3/1975 | Alfidi et al. | 128/345 |
| 3,952,747 | 4/1976 | Kimmell | 128/1 R |
| 4,425,908 | 1/1984 | Simon | 128/345 X |

OTHER PUBLICATIONS

Driller et al.–Med & Biolog Engr. Nov. 1976, vol. 14, No. 6, pp. 629-635.
Gianturco et al.–Radiology–vol. 137, No. 3, pp. 835–837, Dec. 1980.

*Primary Examiner*—Dalton L. Truluck
*Attorney, Agent, or Firm*—Woodard, Weikart, Emhardt & Naughton

[57] ABSTRACT

A blood clot filter which is particularly suited for filtering emboli from blood circulating through the inferior vena cava. The filter is comprised of a number of strands of shape memory wire which are interconnected and wadded together to form a curly wire mesh. The wire strands may be substantially straightened in order to permit insertion of the filter within the lumen of an angiography catheter. The filter includes a number of projections which serve as an anchoring means for anchoring the filter at a suitable body location within the inferior vena cava. One of the strands of wire includes a zig-zag which permits the attachment of the filter to the stretched distal end of a helically formed wire guide, thereby permitting the filter to be urged longitudinally through the lumen of the catheter for positioning within the inferior vena cava. In order to implant the filter, a percutaneous catheterization is made using a femoral approach. Once inside the inferior vena cava, the filter is pushed out of the catheter using the wire guide. The filter automatically expands to fill the passageway of the inferior vena cava without causing substantial occlusion thereof.

14 Claims, 18 Drawing Figures

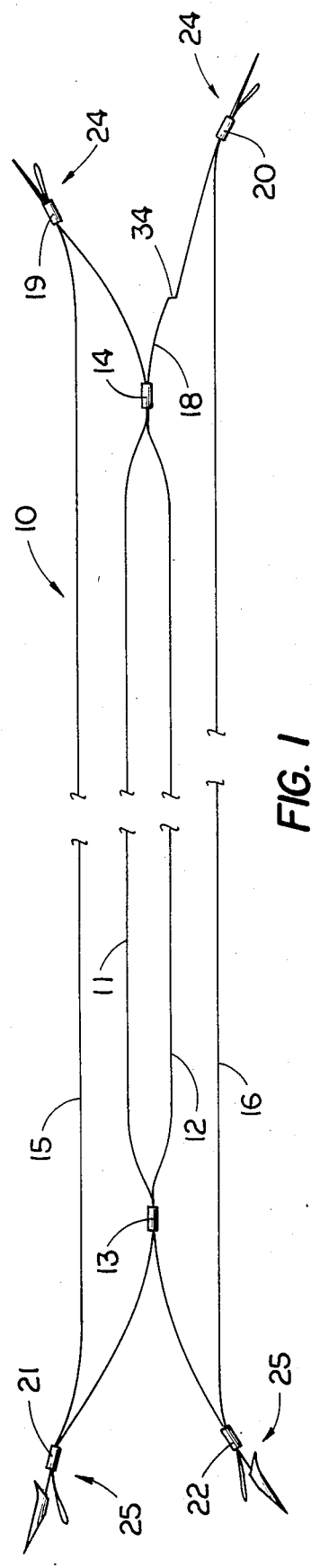
FIG. 1
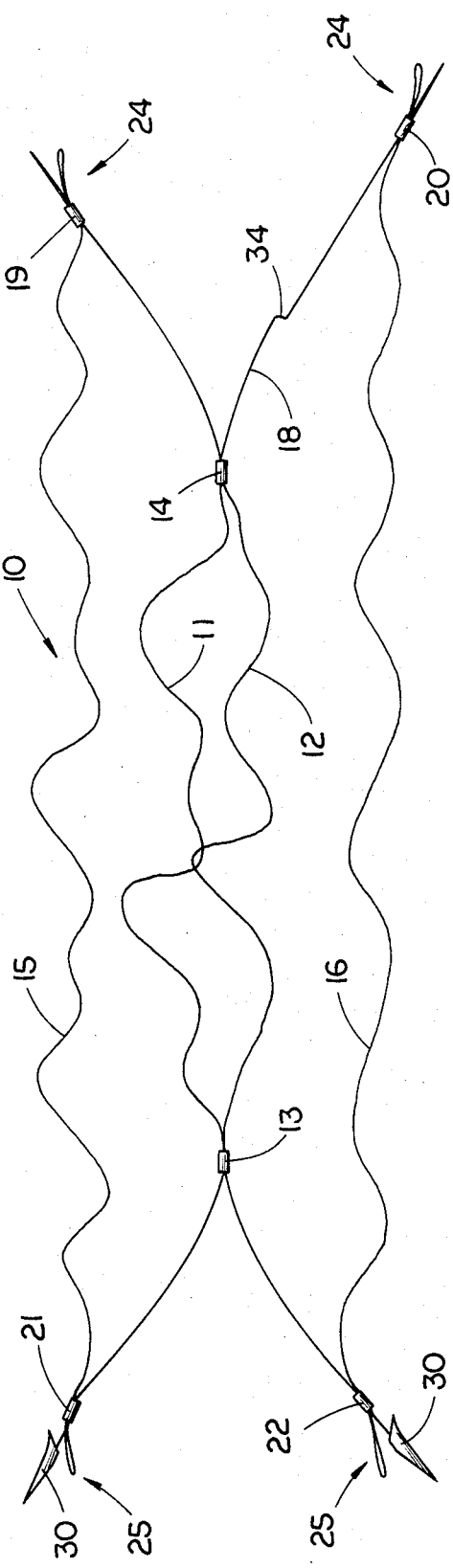
FIG. 2
FIG. 3A
FIG. 3B

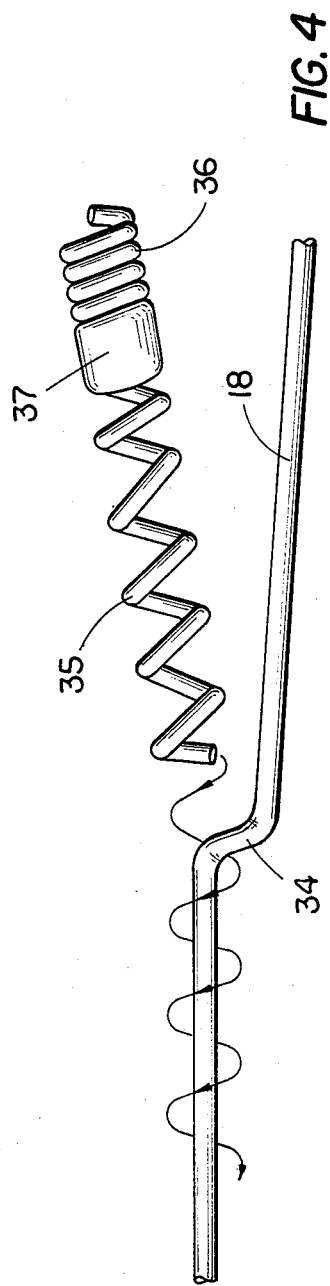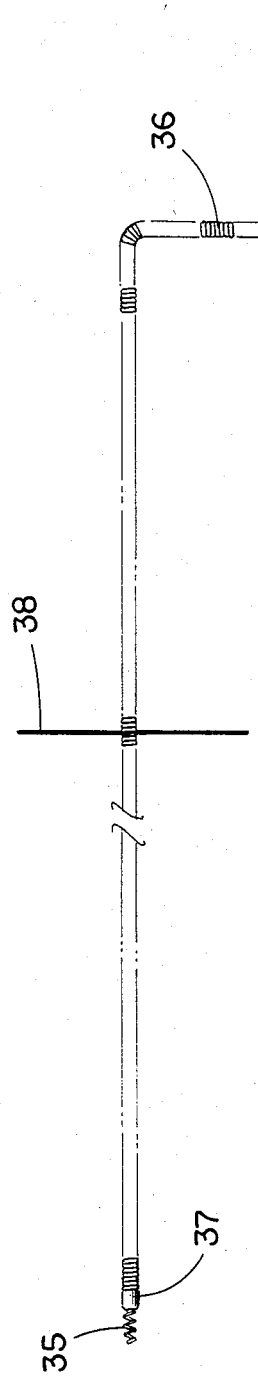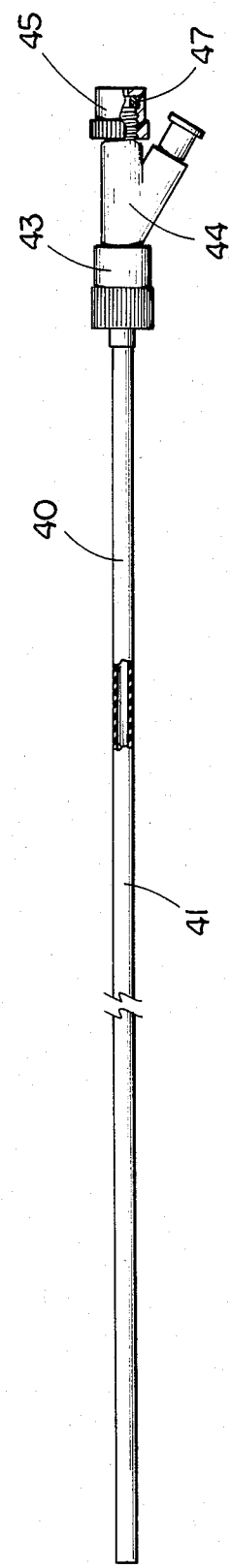

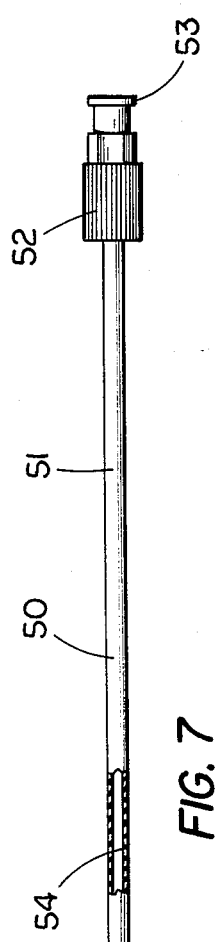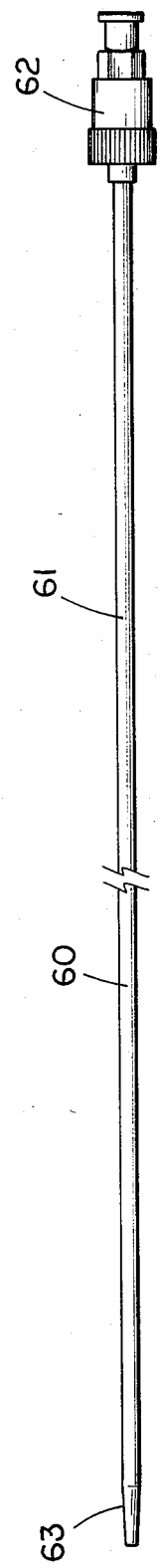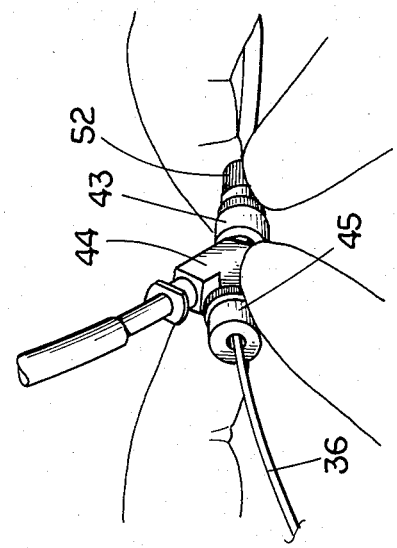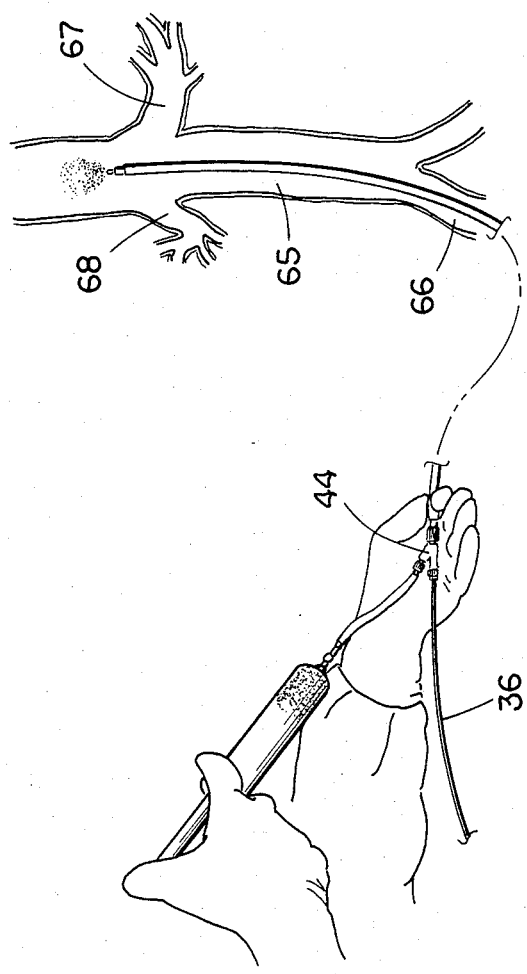
FIG. 7
FIG. 8
FIG. 9
FIG. 10

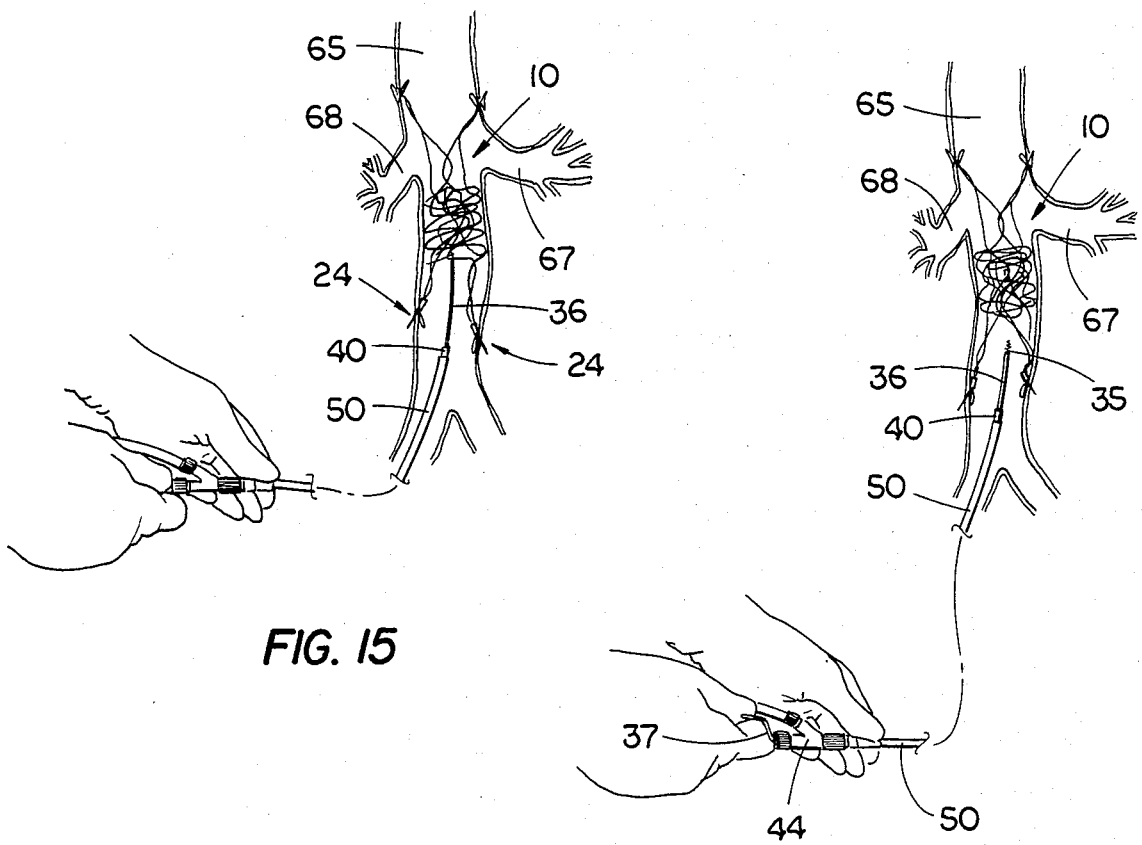
FIG. 15
FIG. 16
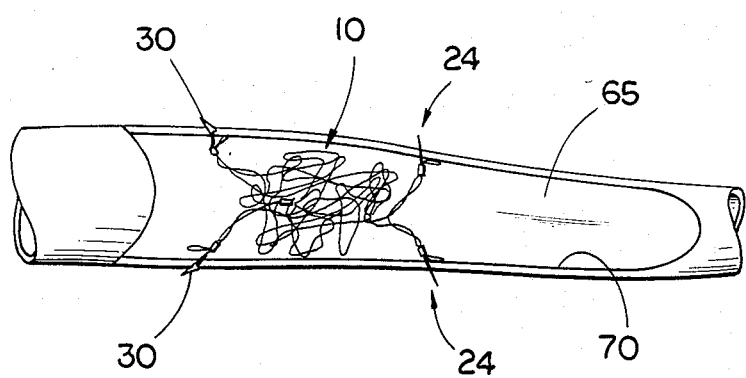
FIG. 17

EXPANDABLE BLOOD CLOT FILTER

BACKGROUND OF THE INVENTION

1. Field of the Invention

The invention relates generally to devices and methods for filtering emboli from blood circulating within a blood vessel, and more particularly, to methods and devices for vena cava filters inserted by the femoral vein approach.

2. Description of the Prior Art

The presence of emboli within the body's circulatory system presents a serious health hazard which can often become life endangering, such as when an embolus travels into the lungs (pulmonary embolus). Most commonly, these emboli are formed in the lower extremitites, especially in patients suffering from phlebitis, patients recovering from surgery, and also non-ambulatory patients who must endure long periods of muscular inactivity. Blood clots or emboli that are formed in the lower extremities, such as the legs, must travel through the inferior vena cava in order to reach the heart, where the emboli are then pumped into the lungs becoming pulmonary embolisms.

One technique used in the prior art which served to prevent emboli from traveling into the lungs and becoming pulmonary embolisms involves the ligation of the vena cava in order to block the passage of any emboli. This technique also prevents the flow of blood through the vena cava, thus requiring the development of collateral circulation to provide passageways for satisfactory blood circulation to the heart. Because of the many disadvantages inherent in performing the major surgery required for the ligation of the vena cava, other methods have been developed.

One of these methods, disclosed in U.S. Pat. No. 3,834,394 to Hunter et al., involves a detachable balloon attached to the distal end of a catheter. The balloon and catheter are inserted by making a surgical incision in one of the veins of the neck and then using the catheter to position the balloon within the inferior vena cava. Once detached, the balloon occludes the inferior vena cava entirely, thus preventing all blood flow. While this method avoids major surgery, it still requires a surgical incision to be performed. Further, since this method also requires total occlusion of the inferior vena cava, the patient is very weak until collateral circulation eventually develops around the balloon. Hopefully, by this time, the reason for the existence of an embolism problem has past. Since this method requires the inferior vena cava to be entirely occluded, it is only used in extreme cases.

Another method for preventing pulmonary embolisms, but which does not require total occlusion of the inferior vena cava, involves implanting a filter device constructed similar to the frame of an umbrella as a permanent implant within the inferior vena cava. Such a device is disclosed in U.S. Pat. No. 3,540,431 to Mobin-Uddin. While the Mobin-Uddin device avoids total occlusion, its design does partially occlude the inferior vena cava. In addition, the Mobin-Uddin device does not avoid the disadvantages of the other previous methods in that it still requires a small incision to be made in the jugular vein and passage of the filter through the heart in order to be positioned within the inferior vena cava. This device, therefore, suffers the inherent disadvantages associated with a jugular vein approach, partial occlusion of the inferior vena cava and surgery.

Experience with devices similar to those disclosed above has demonstrated the desirability of a device which would not only serve to trap the migration of emboli but which would also not obstruct caval blood flow at any time, thus eliminating the requirement of collateral circulation. Ideally, the device should be constructed in order that it may be implanted by a femoral approach, as opposed to a more difficult jugular vein approach. Additionally, the device should not create additional emboli and should be capable of relatively secure anchoring at the desired body location within the blood vessel.

U.S. Pat. No. 3,952,747 to Kimmel discloses a blood vessel filter and filter insertion instrument which overcomes some of the disadvantages of the previous references. The Kimmel reference discloses a method which allows the filter to be inserted by a femoral approach, although this method still requires surgery in order to effect insertion. The device disclosed in the Kimmel reference uses a filter comprised of a plurality of wire legs in a generally conical array and joined at their convergent ends to an apical hub. The wire legs each include a plurality of bends intermediate along their length which decrease the solids by-pass capability of the filter without substantially occluding the blood vessel. Thus, the Kimmel reference discloses a blood clot filter which avoids the collateral circulation requirement inherent in the previous devices and the disadvantages associated with a jugular or other neck vein approach.

The filter disclosed in the Kimmel reference, however, still suffers certain disadvantages. One disadvantage, which is inherent in the conical design of the filter, is that the anchoring means must be placed at the divergent ends of the wire legs in order to securely anchor the device within the blood vessel. As a result, the divergent ends of the wire legs must be substantially collapsed and sheathed in order for the filter to be inserted within the blood vessel, and a fairly complicated means must be used to unsheath the filter for implantation within the blood vessel. Thus, the filter disclosed in the Kimmel reference inherently cannot be inserted within a blood vessel using normal percutaneous catheterization techniques. In order to use the filter disclosed in the Kimmel reference, it is necessary to perform a venotomy or incision of the blood vessel, for its insertion therein. Further, once insertion within the blood vessel is effected, a syringe type ejection means is required in order to be able to unsheath the filter for implantation.

Other references which disclose devices providing partial or total occlusion of a blood vessel in order to prevent emboli from reaching the lungs are U.S. Pat. No. 3,334,629 to Cohn and U.S. Pat. No. 3,795,246 to Sturgeon.

The device and method disclosed in the present invention overcomes the disadvantages associated with the prior art by employing a non-occlusive filter which is designed to be inserted using normal percutaneous catheterization techniques combined with a femoral approach. Thus, the need for surgery is totally obviated as well as the need for a syringe, such as disclosed in the Kimmel reference. A further improvement offered by the filter of the present invention and not found in any of the previous references involves its wire mesh design. The wire mesh design permits the filter to become firmly attached not only at the initial anchor points at the ends of the wires, but also along portions of wire length which directly abut the intimal wall of the blood vessel. The contact of the filter against the vessel wall along these portions permits endothelization and fibrotic encasement of the filter to the intimal wall surface to an extent not previously attainable using previous designs.

Accordingly, it is an object of the present invention to provide a blood clot filter which may be implanted using normal percutaneous catheter techniques combined with a femoral approach.

It is a further object of the present invention to provide a blood clot filter which is designed to be placed within the inferior vena cava, well below the renal veins.

It is a yet further object of the present invention to provide a blood clot filter which will not obstruct blood flow within the blood vessel at any time.

It is a still further object of the present invention to provide a blood clot filter which will not create additional emboli after implantation.

An additional object of the present invention to provide a blood clot filter which is capable of being securely anchored within the blood vessel.

These and other objects and advantages of the present invention will become more apparent in the following figures and detailed description.

SUMMARY OF THE INVENTION

One embodiment of the present invention provides a blood clot filter for positioning within the fluid passageway of a blood vessel in a human body. The blood clot filter is comprised of a shape memory wire capable of assuming two functional positions. In its first position the wire is substantially straightened to permit retention of the filter in the lumen of an angiography catheter. In its second position the wire is substantially contracted along its length in order to form a curly wire mesh. The potential energy which is stored in the wire in its straightened position is sufficient to force the wire in its contracted position into urging contact with the intimal wall of a blood vessel at a multiplicity of contact points. The contact of the filter with the intimal wall of the blood vessel aids in the anchoring of the filter at a predetermined body location within the blood vessel and also encourages endothelization and fibrotic encasement at the contact points. The wire has a sufficiently small diameter to prevent substantial occlusion of the blood vessel when the filter is implanted.

BRIEF DESCRIPTION OF THE DRAWINGS

FIG. 1 is a fragmentary elevation view of the blood clot filter of the present invention in a totally straightened position.

FIG. 3A is an enlarged detail view of one of the two forward anchoring means in the blood clot filter of the present invention.

FIG. 3B is an enlarged detail view of one of the two rearward anchoring means in the blood clot filter of the present invention.

FIG. 4 is an enlarged fragmentary perspective view which illustrates how the wire guide of the present invention is attached and detached from the blood clot filter in order to effect implantation of the blood clot filter within a body blood vessel, such as the inferior vena cava.

FIG. 5 is a fragmentary view of the wire guide handle of the present invention.

FIG. 7 is a fragmentary view of the catheter sheath of the present invention.

FIG. 8 is a fragmentary view of the dilator of the present invention.

FIGS. 9-16 are diagrammatic views illustrating various steps in performing a catheterization of the inferior vena cava using the clot filter assembly of the present invention to implant the blood clot filter therein.

FIG. 17 is a perspective view of a portion of the inferior vena cava and having a section removed to show the configuration of the blood clot filter in its implanted and anchored position within the inferior vena cava.

DESCRIPTION OF THE PREFERRED EMBODIMENT

Figure 11:
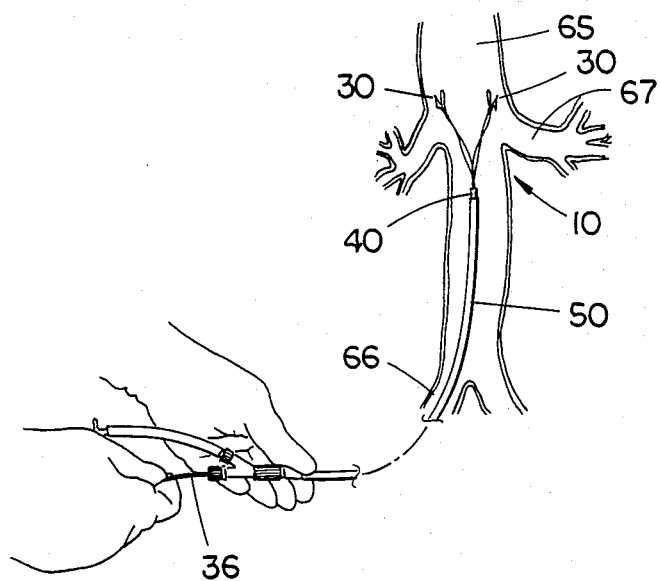
Figure 12:
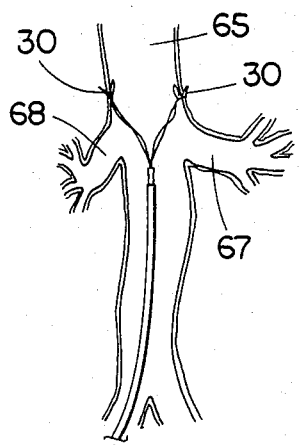

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
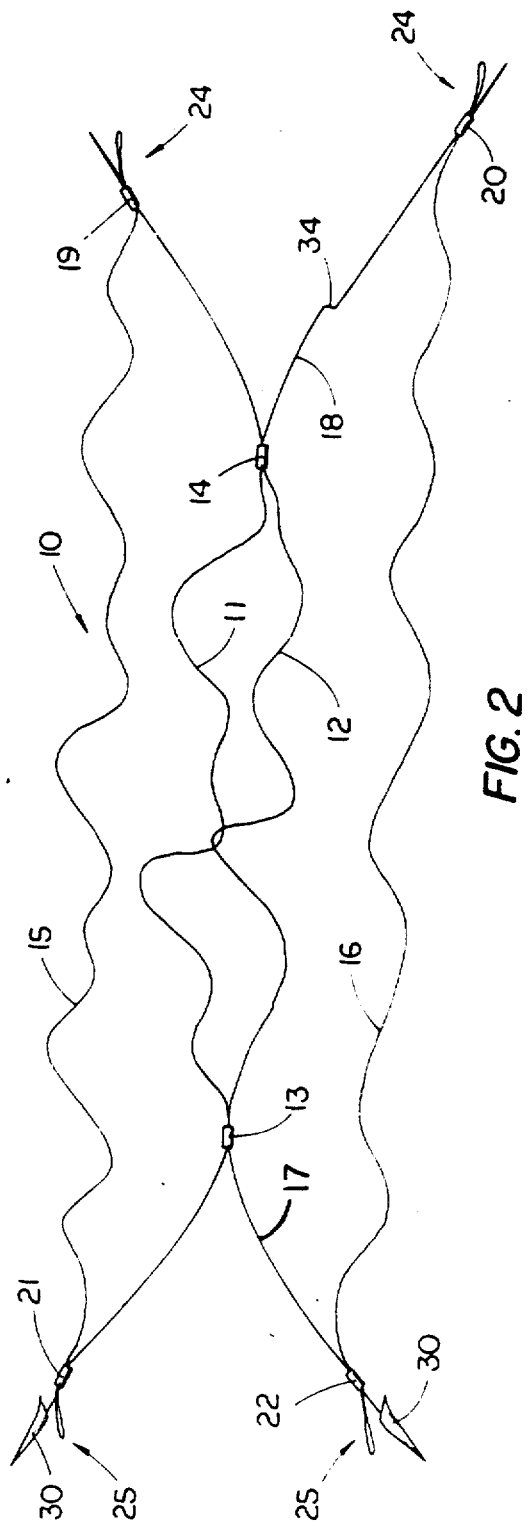
FIG. 2 is an elevation view of the blood clot filter of the present invention in a partially straightened position.

Referring now to the drawings, FIGS. 1 and 2 show the blood clot filter of the clot filter assembly of the present invention generally designated at 10. Filter 10 is shown in a totally straightened position in FIG. 1 with its wire strands slightly spaced apart so that the construction of filter 10 may be more clearly seen. FIG. 2 shows filter 10 in a partially straightened but also somewhat curled position. It should be understood that filter 10 would normally assume the shape of a curly wire mesh unless external forces are employed to straighten the wire strands. It is also to be understood that filter 10 would be provided to the physician in a prepackaged assembly additionally including a cartridge catheter and a wire guide handle, both of which will be more fully described herein.

Filter 10 includes six strands of stainless steel wire which are connected to each other in the following manner. Innermost strands 11 and 12 are mutually attached at both ends by crimps 13 and 14. Innermost strands 11 and 12 are approximately 25 centimeters in length and are made from 0.007 inch diameter coil wire. Outermost strands 15 and 16 are located oppositely of innermost strands 11 and 12 and are each connected thereto at both ends by wire strands 17 and 18. Outermost strands 15 and 16 are approximately 38 centimeters in length and are made from 0.007 inch diameter coil wire. Wire strand 17 serves to connect outermost strands 15 and 16 with innermost strands 11 and 12 at the distal end of filter 10. In a similar manner, wire strand 18 connects outermost strands 15 and 16 with innermost strands 11 and 12 at the proximal end of filter 10. Wire strand 17 is secured to outermost strands 15 and 16 by crimps 21 and 22, respectively and to innermost strands 11 and 12 by crimp 13. In a similar fashion, wire strand 18 is secured to outermost strands 15 and 16 by crimps 19 and 20, respectively, and to innermost strands 11 and 12 by crimp 14. Wire strands 17 and 18 are approximately 10 centimeters in length and are made from 0.010 inch diameter stainless steel coil wire. Crimps 19–22 are made from 3 mm. of 22 GTW cannula while crimps 13 and 14 are made from 3 mm. lengths of 19.5 GTW cannula. Innermost strands 11 and 12, and outermost strands 15 and 16 are made from a shape memory material, such as spring temper stainless steel.

During manufacture, wire strands 11, 12, 15 and 16 are curled in different directions and wadded together to form a curly wire mesh. Because of their shaped memory construction, innermost strands 11 and 12 and outermost strands 15 and 16 may be straightened out at their ends substantially as shown in FIG. 1 for loading into the lumen of a Teflon angiography catheter cartridge. It may be noted that once loaded within the catheter, the spring bias inherent within the wire strands will cause some curling thereof. Further curling is, of course, restrained by the intimal wall of the catheter cartridge. Thus, it is the spring bias inherent in the shape memory construction which allows filter 10 to expand radially outward as innermost wire strands 11 and 12 and outermost wire strands 15 and 16 contract along their lengths upon insertion in a body blood vessel, as will be more fully explained herein.

Means for anchoring filter 10 within a body blood vessel, such as the inferior vena cava, is generally designated at 24 and 25, the details of their construction being more clearly understood by reference FIGS. 2, 3A and 3B. It is to be understood that anchoring means 24 is located at the rearward end of both wire strands 15 and 16, while anchoring means 25 is located at the forward end of both wire strands 15 and 16. Anchoring means 24 differs from anchoring means 25 due to the presence of a barb 30 whose purpose will become fully apparent hereinafter. In the preferred embodiment, the anchoring means 24 and 25 at the ends of outermost wire strand 15 are longitudinally staggered from the corresponding anchoring means 24 and 25 at the ends of outermost wire strand 16. This permits the easy loading of filter 10 within the lumen of a catheter cartridge such as will be more fully described herein.

Referring particularly to FIGS. 2 and 3B, the details of construction of the rearward anchoring means 24 will now be described. It is to be understood that while only the rearward anchoring means 24 at the end of outermost wire strand 15 is described, the rearward anchoring means 24 at the end of outermost wire strand 16 is of a similar construction. It is seen that rearward anchoring means 24 includes a length 26 of outermost wire strand 15 located at the rearward end thereof. Length 26 is approximately one centimeter in length and has a sharp end point 27 which is meant to enter the wall of a blood vessel in the manner shown in FIG. 3B. In order to prevent too deep penetration of anchoring means 24 through the blood vessel, a loop 28 of wire formed from wire strand 18 is positioned adjacent length 26. Loop 28 extends approximately 7 mm along length 26, crimp 19 serving to secure the end of loop 28.

It is to be understood that there are two forward anchoring means 25 at the forward end of filter 10. As previously mentioned, forward anchoring means 25 is of a similar construction to anchoring means 24 except that a barb 30 is received over the end length of wire corresponding to length 26 of anchoring means 24. The purpose of barb 30 is to provide a more secure anchor at the down stream end of filter 10 and thereby ensure long term patentcy of the filter. Barbs 30 are secured to the forward ends of the outer most wire strands 15 and 16 by soldering. FIG. 3A shows the construction of one of the two barbs 30 in detail. Each of the barbs 30 have a lancet bevelled portion 31 which faces outwards of filter 10 and a hooked portion 32 at the inwards facing end. Hooked portion 32 serves to prevent barb 30 from becoming dislodged from the body blood vessel once penetration thereof has been made. Each of the barbs 30 is constructed from 6 mm. to 0.028 inch diameter cannula.

Referring again to FIG. 2, wire strand 18 is shown having a zig-zag 34 therein which is located approximately 7 mm. rearward of crimp 14. The purpose of zig-zag 34 will become more clear by reference to FIG. 4 which shows zig-zag 34 and the distal portion 35 of wire guide handle 36 of the present invention immediately adjacent thereto. As seen in FIG. 4, zig-zag 34 permits the attachment of wire guide handle 36 for remote-controlled movement of filter 10. Wire guide handle 36 is made from a length of 0.018 inch diameter mandrel wire. As seen in FIG. 5, the proximal end of wire guide handle 36 forms a handle portion 37 which facilitates rotation of wire guide handle 36, while the distal portion 35 consists of a helically formed length of 0.010 inch wire coil. Distal portion 35 is made by merely extending or stretching in a longitudinal direction the distal portion 35 of wire guide handle 36 which has a conventionally known helical construction. The innermost end 37 of distal portion 35 is then silver soldered for additional strength. The stretched distal portion 35 of wire guide handle 36 may then be screwed on to wire strand 18 for attachment thereto at zig-zag 34 by clockwise rotation of wire guide handle 36. In order to control depth of body insertion of wire guide handle 36, sutures such as seen at 38 may be tied thereto at measured locations.

It is easily perceived that once distal portion 35 of wire guide handle 36 has been attached to wire strand 18 at zig-zag 34, it is possible to move wire strand 18 and thus also filter 10 longitudinally by merely pushing or pulling on wire guide handle 36. Also, in order to disattach wire guide handle 36 from filter 10 it is only necessary to unscrew distal portion 35 of wire guide handle 36 from zig-zag 34 of wire strand 18 by counter-clockwise rotation. Zig-zag 34 is formed by double bending wire strand 18 so that zig-zag 34 extends substantially perpendicular to the length of filter 10.

Figure 6:
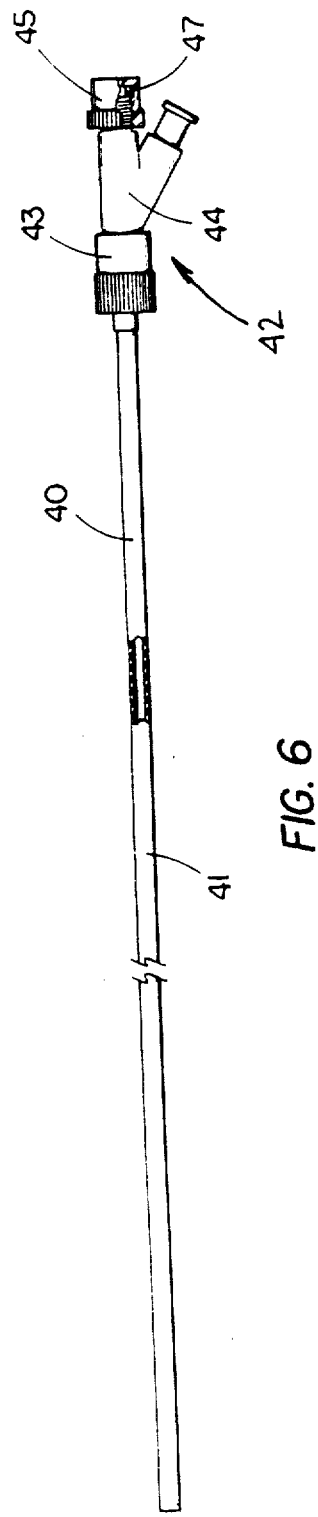
FIG. 6 is a fragmentary view, partially in section, of the cartridge catheter of the present invention.

FIGS. 6–8 depict the cartridge catheter 40, sheath 50, and dilator 60 of the clot filter assembly of the present invention. FIG. 6 shows cartridge catheter 40 including a tubular portion 41 which is approximately 40 centimeters in length and is made from 8.0 French size Teflon tubing having an outer diameter of 0.105" and an inner diameter of 0.073". Tubular portion 41 is connected to a rear assembly 42 which includes coupling member 43, side port fitting 44 and cap 45. Fitting 44 is externally threaded at both ends for attachment to coupling member 43 and cap 45. Coupling member 43 has an internally threaded portion 46 along its forward end which permits coupling to the distal end of sheath 50 in a manner which will be described more fully herein. Cap 45 includes a latex washer 47 which permits cartridge catheter 40 to be firmly held in place over wire guide handle 36, the purpose of which will become more apparent later. This is accomplished by tightening cap 45 onto side port fitting 44 so as to compress latex washer 47 against wire guide handle 36.

Referring now to FIG. 7, sheath 50 is shown to include a tubular portion 51 which is fixedly attached to connector cap 52. Connector cap 52 includes a male coupling means which consists of a collar 53 which serves to permit coupling between sheath 50 and either cartridge catheter 40 or dilator 60. Sheath 50 has a lumen 54 therein which extends along the entire length of sheath 50. Tubular portion 51 is approximately 37.5 cm. in length and is made from 8.5 French size sheathing having an outer diameter of 0.133" and an inner diameter of 0.113".

Referring now to FIG. 8, dilator 60 is shown including a tubular portion 61 which is fixedly attached at its proximal end to connector cap 62. Connector cap 62 is of similar construction to connector cap 52 of sheath 50, and no further explanation of its construction is necessary. Tubular portion 61 has a dilator tip 63 which extends approximately 0.8 cm. rearwards from the distal end of dilator 60 and serves to facilitate the introduction of sheath 50 within a body blood vessel in performing a catheterization. Tubular portion 61 is approximately 41 cm. in length and is made from 8.0 French size Teflon tubing. Tubular portion 61 has an outer diameter of 0.105" and an inner diameter of 0.073", except along the length of dilator tip 63 which is, of course, gradually smaller as it approaches the distal end of dilator 60.

In order to use the clot filter assembly of the present invention filter 10, wire guide handle 36 and cartridge catheter 40 are provided to the physician preassembled as follows. Filter 10 and wire guide handle 36 are attached in the manner previously described and filter 10 is loaded within the lumen of cartridge catheter 40. Loading filter 10 inside cartridge catheter 40 is accomplished by first straightening the inner most strands 11 and 12 and outermost strands 15 and 16 of filter 10. Of course, filter 10 will contract slightly within the lumen of cartridge catheter 40 as it is loaded therein, however, the lumen of cartridge catheter 40 is sufficiently small to force wire strands 11, 12, 15 and 16 of filter 10 to retain a substantially straight orientation.

FIGS. 9-16 illustrate the steps involved in using the clot filter assembly of the subject invention. In order to place and anchor filter 10 within the inferior vena cava 65, a percutaneous catheterization is performed in the normal manner, the initial insertion being effected with a hollow thin wall needle and wire guide using a femoral approach. The needle and wire guide may be of any conventionally known and suitable type, it being understood that no further description of their construction is necessary for those skilled in the art. Then, with tubular portion 61 of dilator 60 inserted within the lumen of sheath 50 and connector cap 62 threadingly coupled over collar 53 of sheath 50, the sheath and dilator combination is inserted within the femoral vein 66. Once sheath 50 and dilator 60 are properly inserted, the dilator and initial wire guide are removed. Cartridge catheter 40, along with filter 10 and attached wire guide handle 36, is then inserted within the lumen of sheath 50 until coupling member 43 is threadably coupled over collar 53 of sheath 50. As depicted in FIG. 9, sheath 50 and cartridge catheter 40 are thereafter passed under fluoroscopic control to a desired position approximately 1 cm. above the renal veins 67 and 68. Cartridge catheter 40 should be filled with radiopaque medium by injection through side port fitting 44, this being done for visualization purposes. Cap 45 is then unscrewed until wire guide handle 36 is loosened for longitudinal movement within lumen of cartridge catheter 40 (FIG. 10).

Thereupon, as depicted in FIG. 11, and with wire guide handle 36 being held in place, cartridge catheter 40 is pulled rearwardly approximately 4 cm., thereby exposing the two barbs 30. In order to seat the barbs within the inferior vena cava wall, cartridge catheter 40 and wire guide handle 36 are sharply advanced (FIG. 12) as a unit 1 to 2 cm. It has been found that 2 or 3 such jab-like movements will assure firm seating.

Figure 13:
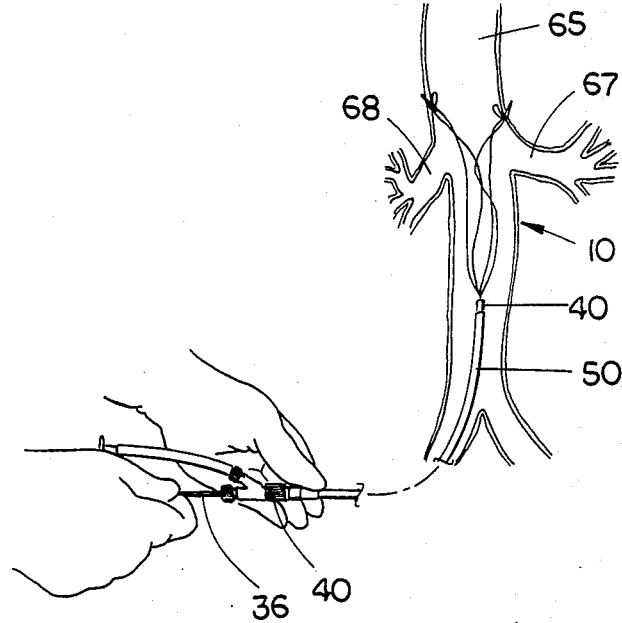

Referring now to FIG. 13, after the barbs 30 are firmly secured, cartridge catheter 40 is withdrawn approximately 8 cm. while wire guide handle 36 is held firmly in place. This places the distal end of cartridge catheter 40 well below renal veins 67 and 68 and in a position from which the remaining portions of filter 10 may be fed into a position within the inferior vena cava below the renal veins.

Figure 14:
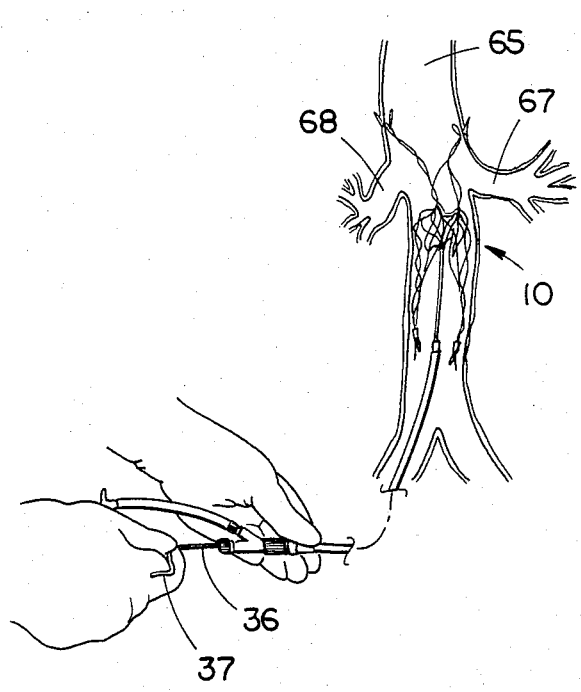

As seen in FIG. 14, the next step requires wire guide handle 36 to be advanced as far as it will go, i.e. up to the first right angle bend of handle portion 37, while firmly holding cartridge catheter 40 in place. This movement feeds the remaining portions of filter 10 into the inferior vena cava 65. Once filter 10 is fully positioned within the inferior vena cava, the rearward anchoring means 24 (FIG. 15) are seated by sharply pulling back cartridge catheter 40 and wire guide handle 36 as a unit, approximately 1-2 cm.

It is to be appreciated that due to the potential energy stored within wire strands 11, 12, 15 and 16 in their substantially straightened position within cartridge catheter 40, filter 10 contracts longitudinally and at the same time expands radially to encompass the entire blood passageway of the inferior vena cava 65. Further radial expansion is, of course, restricted by the intimal wall of the inferior vena cava.

After it has been determined that filter 10 is successfully implanted within the inferior vena cava, it is necessary to separate wire guide handle 36 from filter 10. As depicted in FIG. 16, this is accomplished by turning wire guide handle 36 approximately 20 revolutions to unscrew it from filter 10. Separation can usually be identified by fluoroscopy. If the stretched distal portion 35 catches on any of the wire strands of filter 10, it is only necessary to continue counter-clockwise rotation as wire guide handle 36 is withdrawn in order to free it.

FIG. 17 show filter 10 in its longitudinally contracted and radially expanded position within the inferior vena cava of a human body. It is to be noted that in this position filter 10 is in the shape of a curly wire mesh with spaces therethrough no larger than 3-4 mm. Also, due to the relatively small diameters of the wire strands, filter 10 occupies only a minimal portion of the cross-sectional area of the blood vessel passageway. Thus, filter 10 does not substantially occlude the blood vessel passageway. Also, barbs 30 extend into the intimal wall of the inferior vena cava in such fashion so as to firmly anchor filter 10, thereby ensuring long term patency.

In addition to the anchoring points at barbs 30, FIG. 17 also shows filter 10 in urging contact with the intimal wall 70 of the inferior vena cava 65 at innumerable other points along the lengths of various portions of the wire strands of filter 10. Initially, these points of urging contact do not provide sufficient anchoring to ensure patency of filter 10, thus requiring the anchoring means provided by barbs 30. However, after several weeks endothelization and fibrotic encasement occurs at the points where the wire mesh of filter 10 abuts the intimal wall of the inferior vena cava, and the likelihood of permanent patency is thereafter greatly increased.

While the foregoing description applies to the insertion of filter 10 in the inferior vena cava of a human body using a femoral approach, it is to be understood that the device and method of the subject invention may be used with different techniques such as a jugular approach. The device and method of the subject invention may also be used to effect the filtering of emboli or other obstructions from blood vessels other than the inferior vena cava. Of course, the size and shapes of various elements described herein would have to be varied in order to accomplish such other techniques or uses, but such variations as may be necessary would be well within the skill of those knowledgable in the art.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A blood clot filter for positioning within the fluid passageway of a blood vessel in a human body, comprising:
   a shape memory wire, said wire contractible from a first position wherein said wire is substantially straightened to permit insertion of the filter within the lumen of an angiography catheter, to a second position wherein said wire is contracted along its length to form a curly wire mesh, the potential energy stored in said wire in its first position being sufficient to force said wire into its second position and into urging contact with the intimal wall of said blood vessel at a multiplicity of contact points, thereby aiding the anchoring of said filter at a desired body location within said blood vessel and encouraging endothelization and fibrotic encasement at said contact points, said wire having a sufficiently small diameter to prevent substantial occlusion of said blood vessel when said filter is implanted therein; and
   anchoring means on said wire for anchoring said filter at a determined body location within said blood vessel, said anchoring means including a plurality of sharp projections for penetrating into said intimal wall of said blood vessel;
   said projections being positioned at the opposite ends of said filter, said projections at the forward end of said filter each including a barb sharpened at both ends, said barbs being adapted to pierce the intimal wall of said blood vessel and to hook in place to resist extraction.

2. The apparatus of claim 1 and further comprising: introduction means integral with said wire for facilitating the introduction of said wire into said blood vessel through the lumen of said catheter.

3. The apparatus of claim 1 wherein said anchoring means includes a loop of wire crimped to each projection adjacent each of said barbs and adapted to resist the barb's penetration of the intimal wall an excessive amount.

4. The apparatus of claim 3 wherein said anchoring means includes four projections, two each positioned at opposite ends of said filter, said projections longitudinally staggered at each end to facilitate loading of said filter within said catheter.

5. The apparatus of claim 2 wherein said wire includes a plurality of strands.

6. The apparatus of claim 5 wherein said wire includes four or more strands.

7. The apparatus of claim 6 wherein each strand is connected at both ends to at least one other strand and a plurality of said strands are connected at at least one intermediate point along their lengths.

8. The apparatus of claim 3 wherein said barbs have a length which is less than 1 cm.

9. The apparatus of claim 2 wherein said introduction means is a zig-zag in said wire, said zig-zag providing a surface substantially perpendicular to the length of said wire when said wire is in its first position, thereby permitting said filter to be urged longitudinally through the lumen of said catheter for positioning in said blood vessel.

10. The apparatus of claim 8 wherein said wire is made of tempered stainless steel.

11. The apparatus of claim 9 wherein said wire has a diameter which is less than 0.015 inches.

12. An assembly for performing a catheterization of a blood vessel in a human body in order to filter emboli from blood circulating through said blood vessel, said assembly comprising:
   a catheter sized to be received within the passageway of a blood vessel and inserted therein over said first wire guide;
   a filter expandable radially outwards perpendicular to the length of said filter from a first position wherein said filter is entirely received within the lumen of said catheter to a second position wherein said filter encompasses substantially the entire cross-sectional area within the passageway of said blood vessel;
   a wire guide having a diameter sized to permit said wire guide to be received through the lumen of said catheter, said wire guide including means for urging said filter out an end of said catheter and into a determined body location within the passageway of said blood vessel;
   said wire guide including a helical distal portion which is formed so as to separate the adjacent loops of the helical portion, said helical distal portion being rotatable about its axis to screw the wire guide onto and off of said filter, said filter having a wire portion bent into a Z-shape, said Z-shape being adapted to receive the screwed on wire guide for connecting and disconnecting the wire guide to the filter.

13. The apparatus of claim 12, and further comprising:
   a dilator including a tubular portion having a lumen therethrough, said tubular portion having a tip portion of narrowing cross-section for dilating said blood vessel in order to permit the subsequent insertion of said catheter.

14. The apparatus of claim 13, and further comprising:
   a catheter sheath having a lumen therethrough and sized to be received over said tubular portion of said dilator, said catheter sheath lumen sized to receive said catheter.

* * * * *

UNITED STATES PATENT AND TRADEMARK OFFICE
CERTIFICATE OF CORRECTION

PATENT NO. : 4,494,531

DATED : January 22, 1985

INVENTOR(S) : Cesare Gianturco

It is certified that error appears in the above-identified patent and that said Letters Patent is hereby corrected as shown below:

Column 6, line 60, delete "46"

Column 10, line 29, "said first" should read -- a --.

Column 10, line 38, "a wire" should read -- said wire --.

Figs. 2 and 6, should appear as shown on the attached sheets.

Signed and Sealed this

Fifth Day of August 1986

[SEAL]

Attest:

DONALD J. QUIGG

Attesting Officer

Commissioner of Patents and Trademarks

UNITED STATES PATENT AND TRADEMARK OFFICE

CERTIFICATE EXTENDING PATENT TERM
UNDER 35 U.S.C. 156

Patent No.     :  4,494,531

Dated          :  January 22, 1985

Inventor(s)    :  Cesare Gianturco

Patent Owner   :  Cook, Incorporated

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

459 DAYS with all rights pertaining thereto as provided by 35 USC 156 (b).

I have caused the seal of the Patent and Trademark Office to be affixed this 25th day of April 1990.

Harry F. Manbeck, Jr.
Assistant Secretary and Commissioner
of Patents and Trademarks